US011952631B2

(12) United States Patent
Todt et al.

(10) Patent No.: US 11,952,631 B2
(45) Date of Patent: Apr. 9, 2024

(54) DIAGNOSTICS AND THERAPY FOR HUMAN RESPIRATORY SYNCYTIAL VIRUS

(71) Applicants: MEDIZINISCHE HOCHSCHULE HANNOVER, Hannover (DE); TWINCORE ZENTRUM FÜR EXPERIMENTELLE UND KLINISCHE INFEKTIONSFORSCHUNG GMBH, Hannover (DE); TECHNISCHE UNIVERSITÄT DRESDEN, Dresden (DE)

(72) Inventors: Daniel Todt, Hannover (DE); Sibylle Haid, Hannover (DE); Martin Wetzke, Hannover (DE); Gesine Hansen, Hannover (DE); Chris Lauber, Dresden (DE); Lars Kaderali, Greifswald (DE); Thomas Pietschmann, Hannover (DE)

(73) Assignees: MEDIZINISCHE HOCHSCHULE HANNOVER, Hannover (DE); TWINCORE ZENTRUM FÜR EXPERIMENTELLE UND KLINISCHE INFEKTIONSFORSCHUNG GMBH, Hannover (DE); TECHNISCHE UNIVERSITÄT DRESDEN, Dresden (DE)

( * ) Notice: Subject to any disclaimer, the term of this patent is extended or adjusted under 35 U.S.C. 154(b) by 414 days.

(21) Appl. No.: 16/754,390

(22) PCT Filed: Oct. 9, 2018

(86) PCT No.: PCT/EP2018/077385
§ 371 (c)(1),
(2) Date: Apr. 8, 2020

(87) PCT Pub. No.: WO2019/072789
PCT Pub. Date: Apr. 18, 2019

(65) Prior Publication Data
US 2020/0283848 A1 Sep. 10, 2020

(30) Foreign Application Priority Data

Oct. 9, 2017 (EP) .................... 17195522

(51) Int. Cl.
C12N 15/11 (2006.01)
A61K 31/7105 (2006.01)
A61K 48/00 (2006.01)
C12N 15/113 (2010.01)
C12Q 1/6883 (2018.01)

(52) U.S. Cl.
CPC ........ C12Q 1/6883 (2013.01); A61K 31/7105 (2013.01); A61K 48/005 (2013.01); C12N 15/1131 (2013.01); C12Q 2600/118 (2013.01); C12Q 2600/156 (2013.01)

(58) Field of Classification Search
CPC .................................. C12N 15/1131
See application file for complete search history.

(56) References Cited

U.S. PATENT DOCUMENTS

2012/0101005 A1* 4/2012 Tatnell ............... G01N 33/5073
435/7.1
2015/0104446 A1 4/2015 Polack et al.

FOREIGN PATENT DOCUMENTS

WO 2011123945 A1 10/2011
WO 2012169887 A2 12/2012
WO 2013170215 A1 11/2013

OTHER PUBLICATIONS

Ehteshami et al, Nucleotide Substrate Specificity of AntiHepatitis C Virus Nucleoside Analogs for Human Mitochondrial RNA Polymerase, Antimicrobial Agents and Chemotherapy, May 2017, vol. 61, issue 8: 1-8 (Year: 2017).*
Bouillier et al, The Interactome analysis of the Respiratory Syncytial Virus protein M2-1 suggests a new role in viral mRNA metabolism posttranscription, Scientific Reports, 2019, 9: 15258, pp. 1-13 (Year: 2019).*
NCBI Gene: "ss159737753" dbSNP, pp. 1-1 (Jul. 10, 2009) https://www.ncbi.nlm.nih.gov/projects/SNP/snp_ss.cgi?subsnp_id=159737753.
Ciencewicki et al. "A genetic model of differential susceptibility to human respiratory syncytial virus (RSV) infection." The FASEB Journal 28(4): 1947-1956 (2014).
Stark et al. "Genomewide association analysis of respiratory syncytial virus infection in mice." Journal of Virology 84(5): 2257-2269 (2010).
Tal et al. "Association between common Toll-like receptor 4 mutations and severe respiratory syncytial virus disease." The Journal of Infectious Diseases 189(11): 2057-2063 (2004).
Lu et al. "Association of interleukin 8 single nucleotide polymorphisms with the susceptibility to respiratory syncytial virus infection." Zhonghua er ke za zhi= Chinese Journal of Pediatrics 45.2 (2007): 100-104 [English Abstract].

* cited by examiner

Primary Examiner — Ekaterina Poliakova-Georgantas
(74) Attorney, Agent, or Firm — NIXON PEABODY LLP; Mark J. Fitzgerald; Nicole D. Kling

(57) ABSTRACT

The present invention pertains to a method for the identification of genetic variants that are associated with the severity of an infectious disease. The invention further pertains to a set of genetic factors associated with the severity of Human respiratory syncytial virus (HRSV) infection, for example in human infants. The genetic polymorphisms identified according to the present invention are for use in the diagnostic of infectious diseases and patient stratification in order to avoid or reduce the occurrence of fatal events during infection or to elect the most appropriate therapeutic approach to treat the disease.

Figure 1:
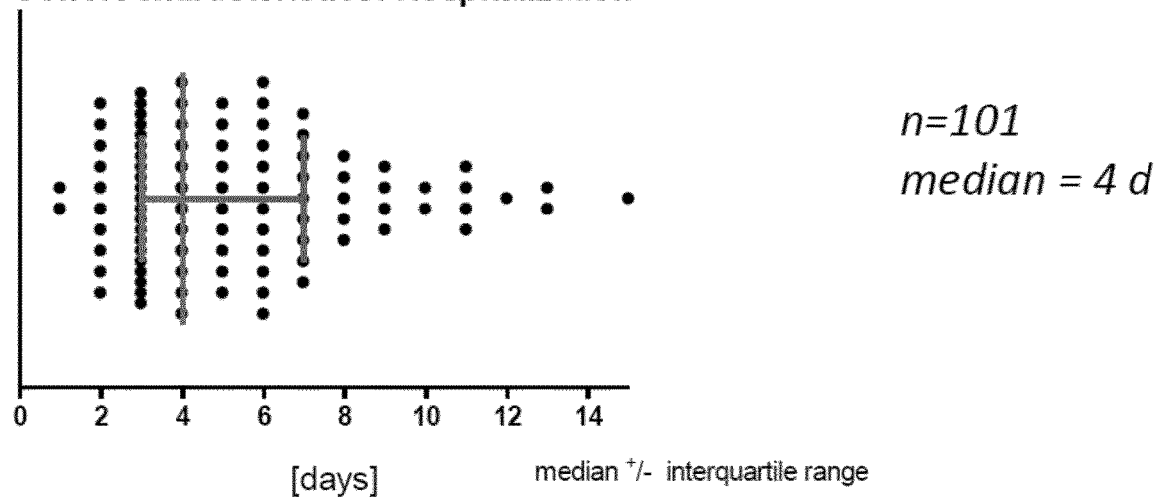
Figure 1:
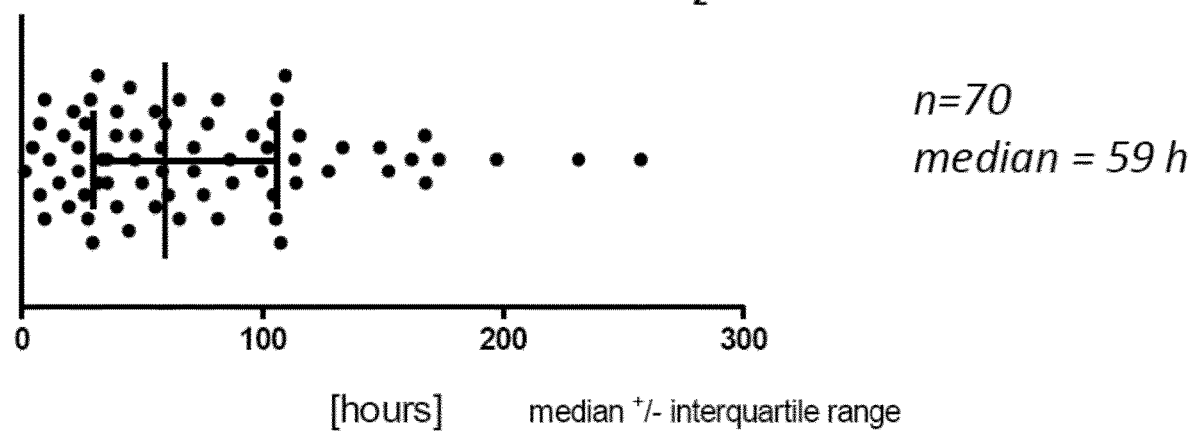

3 Claims, 7 Drawing Sheets
Specification includes a Sequence Listing.

SEQUENCE LISTING

```
<160> NUMBER OF SEQ ID NOS: 5

<210> SEQ ID NO 1
<211> LENGTH: 24
<212> TYPE: DNA
<213> ORGANISM: homo sapiens

<400> SEQUENCE: 1
tgctgctgct gctgctgctg ctgc                                      24

<210> SEQ ID NO 2
<211> LENGTH: 21
<212> TYPE: DNA
<213> ORGANISM: homo sapiens

<400> SEQUENCE: 2
tgctgctgct gctgctgctg c                                         21

<210> SEQ ID NO 3
<211> LENGTH: 27
<212> TYPE: DNA
<213> ORGANISM: homo sapiens

<400> SEQUENCE: 3
tgctgctgct gctgctgctg ctgctgc                                   27

<210> SEQ ID NO 4
<211> LENGTH: 15
<212> TYPE: DNA
<213> ORGANISM: homo sapiens

<400> SEQUENCE: 4
tgctgctgct gctgc                                                15

<210> SEQ ID NO 5
<211> LENGTH: 12
<212> TYPE: DNA
<213> ORGANISM: homo sapiens

<400> SEQUENCE: 5
tgctgctgct gc                                                   12
```

DIAGNOSTICS AND THERAPY FOR HUMAN RESPIRATORY SYNCYTIAL VIRUS

CROSS-REFERENCE TO RELATED APPLICATIONS

This application is a 35 U.S.C. § 371 National Phase Entry Application of International Application No. PCT/EP2018/077385 filed Oct. 9, 2018, which claims the benefit of EP Application No. 17195522.2 filed Oct. 9, 2017, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Apr. 7, 2020, is named SEQ-listing-047260-097210USPX.txt and is 1,194 bytes in size.

FIELD OF THE INVENTION

The present invention pertains to a method for the identification of genetic variants that are associated with the severity of an infectious disease. The invention further pertains to a set of genetic factors associated with the severity of Human respiratory syncytial virus (HRSV) infection, for example in human infants. The genetic polymorphisms identified according to the present invention are for use in the diagnostic of infectious diseases and patient stratification in order to avoid or reduce the occurrence of fatal events during infection or to elect the most appropriate therapeutic approach to treat the disease.

DESCRIPTION

RSV infection is the leading cause of infant hospitalization in industrialized countries. Following primary RSV infection, which generally occurs under the age of 2 years, immunity to RSV remains incomplete, and reinfection can occur. Furthermore, RSV can cause serious disease in the elderly and is in general associated with higher mortality than influenza A in non-pandemic years (Falsey et al., 1995). The WHO-estimated global annual infection rate in the human population is estimated at 64 million cases, with a mortality figure of 160000; in the US alone, from 85000 to 144000 infants are hospitalized each year as a consequence of RSV infection (available on the world wide web at who.int/vaccine_research/diseases/ari/en/index2.html update 2009). RSV belongs to the family Paramyxoviridae, subfamily Pneumovirinae, genus *Pneumovirus*; in human, there are two subgroups, A and B. Apart from the human RSV, there is a bovine variant. The genome of human RSV is approximately 15200 nucleotides long and is a negative-sense RNA molecule. The RSV genome encodes 11 known proteins: Glycoprotein (G), Fusion protein (F), Small hydrophobic protein (SH), Nucleoprotein (N), Phosphoprotein (P), Large protein (L), Matrix protein (M), M2 ORF-1 protein (M2-1), M2 ORF-2 protein (M2-2), Nonstructural protein 1 (NS1) and Nonstructural protein 2 (NS2). G, F and SH are transmembrane surface proteins; N, P, L, M, M2-1 are nucleocapsid associated proteins and NS1 and NS2 are non-structural proteins. The status of M2-2 as a structural or nonstructural protein is unknown. (Hacking and Hull, 2002). The RSV subgroups show differences in the antigenic properties of the G, F, N and P proteins (Ogra, 2004).

RSV infection is followed by the formation of specific IgG and IgA antibodies detectable in the serum and some other body fluids. Several studies have demonstrated that antibody responses are mainly directed to the major RSV transmembrane proteins F and G; only F- and G-specific antibodies are known to have in vitro RSV-neutralizing activity. Antibody responses to the F protein are often cross-reactive between the A and B subgroups, whereas antibody responses to the G protein are subgroup specific (Orga, 2004). Contrary to F and G, the transmembrane protein SH is considered as non-immunogenic (Gimenez et al., 1987; Tsutsumi et al., 1989) and in some vaccine candidates, SH has even been deleted in order to obtain a non-revertible attenuated vaccine (Karron et al., 2005). Development of vaccines to prevent RSV infection has been complicated by the fact that host immune responses appear to play a significant role in the pathogenesis of the disease. Early attempts at vaccinating children with formalin-inactivated RSV showed that vaccinated children experienced a more severe disease on subsequent exposure to the virus as compared to the unvaccinated controls (Kapikian et al., 1969). Live attenuated vaccines have been tested, but show often over- or underattenuation in clinical studies (Murata, 2009).

Subunit vaccines, using one immunogenic protein or a combination of immunogenic proteins are considered safer, because they are unable to revert or mutate to a virulent virus. Candidate vaccines based on purified F protein have been developed and were tested in rodents, cotton rats, and humans, and were shown to be safe, but only moderately immunogenic (Falsey and Walsh, 1996; Falsey and Walsh, 1997; Groothuis et al. 1998). In a similar vein, clinical trials with a mixture of F-, G- and M-proteins have been discontinued in phase II (ADISinsight Clinical database). An alternative approach consisted of a recombinant genetic fusion of the antigenic domain of human RSV G protein to the C-terminal end of the albumin-binding domain of the streptococcal G protein (BBG2Na; Power et al., 2001). BBG2Na was investigated up to a phase III clinical trial in healthy volunteers, but the trial had to be stopped due to the appearance of unexpected type 3 hypersensitivity side effects (purpura) in some immunized volunteers (Meyer et al., 2008).

A recent development is the use of chimeric recombinant viruses as vector for RSV antigens. A chimeric recombinant bovine/human parainfluenzavirus type 3 (rB/HPIV-3) was engineered by substituting in a BPIV-3 genome the F and HN genes by the homologous genes from HPIBV-3. The resulting chimeric rB/HPIV-3 strain was then used to express the HRSV F and G genes (Schmidt et al., 2002). This vaccine is currently under clinical investigation.

There are only a limited number of prevention and treatment options available for severe disease caused by RSV. The most widely used intervention is based on passive immunoprophylaxis with a humanized monoclonal antibody that is derived from mouse monoclonal antibody 1129 (Beeler and van Wyke Coelingh, 1989). This antibody is specific for RSV F protein and neutralizes subgroup A and B viruses. The recombinant humanized antibody 1 129 is known as palivizumab (also known as Synagis) and is used for prophylactic therapy of infants that are at high risk of developing complications upon RSV infection. The antibody is administered intramuscularly on a monthly basis in order to lower the risk of RSV infection in infants at risk due to prematurity, chronic lung disease, or hemodynamically significant congenital heart disease (Bocchini et al., 2009).

Some studies have reported acceptable cost-effectiveness ratios for RSV prophylaxis with palivizumab (Prescott et al., 2010).

As there is no approved vaccine on the market, there is still an unmet need for development and availability of a safe and efficient RSV vaccine. Surprisingly, we found that the extracellular part (ectodomain) of the small hydrophobic protein SH, referred to as SHe, can be used safely for vaccination against RSV infection, especially when it is presented on a carrier as an oligomer preferably as a pentamer. Furthermore, polyclonal or monoclonal antibodies, directed against SHe, can also be used prophylactically or therapeutically for prevention or treatment of RSV infection, respectively.

It was therefore an object of the present invention to provide diagnostic options to identify the risk of a severe course of HRSV infection, in particular in immune compromised patients such as the very young and elderly. The invention intends to provide clinicians with an early detection of the risk of severe of fatal disease courses in order to provide quick or preventive therapeutic measures.

The above problem is solved in a first aspect by a method for assessing the risk of an increased sensitivity of a subject to infections with Human respiratory syncytial virus (HRSV) comprising the steps of determining in a sample isolated from said subject the presence of at least one genetic polymorphism selected from table 1 which is indicative of the risk of an increased sensitivity of the subject to infections with HRSV.

Another aspect of the invention pertains to a method for the diagnosis of an increased sensitivity of a subject to infections with Human respiratory syncytial virus (HRSV) comprising the steps of determining in a sample isolated from said subject the presence of at least one genetic polymorphism selected from table 1, which is indicative of the risk of an increased sensitivity of the subject to infections with HRSV.

Another aspect of the invention pertains to a method for identifying a subject having an increased risk of suffering from a severe infection of HRSV comprising the steps of determining in a sample isolated from said subject the presence of at least one genetic polymorphism selected from table 1, which is indicative of the risk of an increased sensitivity of the subject to infections with HRSV.

For the above methods it is preferably that at least one genetic polymorphism is used according to the herein disclosed table 1. However, in certain embodiments of the aspects of the invention it may be advantageous to use combinations of more than one variant of the herein disclosed table 1. Hence, the methods of the invention are preferably involving 2, 3, 4, 5, 6, 7 or 8 or more genetic polymorphisms.

The term "Single nucleotide polymorphism" or "SNP" means a single nucleotide variation in a genetic sequence that occurs at appreciable frequency in the human population. There are millions of SNPs in the human genome. Most commonly, these variations are found in the DNA between genes. When SNPs occur within a gene or in a regulatory region near a gene, they may play a more direct role in disease by affecting the gene's function. SNPs are well known to one of skill in the art and are notably described in the NCBI database dbSNP (www.ncbi.nlm.nih.gov/SNP/). As used herein, the SNP that are concerned by the invention are described as in table 1.

Typically, the methods of the invention are performed by determining the presence or absence, in a homozygous or heterozygous for of at least one risk allele as disclosed in table 1. Preferably in the above-defined methods, it is deduced that the subject has an increased risk to develop fast progression of HRSV infection if said subject is homozygous or heterozygous for at least one risk allele as disclosed in table 1. More particularly it is deduced that the subject who are homozygous for a risk allele has a higher risk to HRSV than a subject who is heterozygous for the risk allele.

In some embodiments of the invention wherein the infection with HRSV is a severe infection with HRSV, preferably associated with one or more complications selected from bronchiolitis, pneumonia, asthma, and recurring HRSV infection, and combinations thereof.

According to the invention the genotype of the single nucleotide polymorphism is tested from a sample obtained from the subject.

A sample is a DNA containing sample preferably, for example selected from a tissue sample or a liquid sample, such as a hair sample, skin sample, or an oral tissue sample, scraping, or wash or a biological fluid sample, preferably saliva, urine or blood. Tissue extracts are obtained routinely from tissue biopsy and autopsy material. Bodily fluids useful in the present invention include blood, urine, saliva or any other bodily secretion or derivative thereof. As used herein "blood" includes whole blood, plasma, serum, circulating epithelial cells, constituents, or any derivative of blood. According to the invention, the presence of the risk allele may be determined by nucleic acid sequencing, PCR analysis or any genotyping method known in the art. Examples of such methods include, but are not limited to, chemical assays such as allele specific hybridization, primer extension, allele specific oligonucleotide ligation, sequencing, enzymatic cleavage, flap endonuclease discrimination; and detection methods such as fluorescence, chemiluminescence, and mass spectrometry.

For example, the presence or absence of said genetic polymorphism may be detected in a RNA or DNA sample, preferably after amplification. For instance, the isolated RNA may be subjected to couple reverse transcription and amplification, such as reverse transcription and amplification by polymerase chain reaction (RT-PCR), using specific oligonucleotide primers that are specific for the polymorphism or that enable amplification of a region containing the polymorphism. According to a first alternative, conditions for primer annealing may be chosen to ensure specific reverse transcription (where appropriate) and amplification; so that the appearance of an amplification product be a diagnostic of the presence of the polymorphism according to the invention. Otherwise, RNA may be reverse-transcribed and amplified, or DNA may be amplified, after which a mutated site may be detected in the amplified sequence by hybridization with a suitable probe or by direct sequencing, or any other appropriate method known in the art. For instance, a cDNA obtained from RNA may be cloned and sequenced to genotype the polymorphism (or identify the allele). Actually numerous strategies for genotype analysis are available. Briefly, the nucleic acid molecule may be tested for the presence or absence of a restriction site. When a base polymorphism creates or abolishes the recognition site of a restriction enzyme, this allows a simple direct PCR genotype the polymorphism. Further strategies include, but are not limited to, direct sequencing, restriction fragment length polymorphism (RFLP) analysis; hybridization with allele-specific oligonucleotides (ASO) that are short synthetic probes which hybridize only to a perfectly matched sequence under suitably stringent hybridization conditions; allele-specific PCR; PCR using mutagenic primers; ligase-PCR, HOT cleavage; denaturing gradient gel electrophoresis (DGGE), temperature denaturing gradient gel electrophoresis (TGGE), single-stranded conformational polymorphism (SSCP) and denaturing high performance liquid chromatography (Kuklin et al, 1997). Direct sequencing may be accomplished by any method, including without limitation chemical sequencing, using the Maxam-Gilbert method; by enzymatic sequencing, using the Sanger method; mass spectrometry sequencing; sequencing using a chip-based technology; and real-time quantitative PCR. Preferably, DNA from a subject is first subjected to amplification by polymerase chain reaction (PCR) using specific amplification primers. However several other methods are available, allowing DNA to be studied independently of PCR, such as the rolling circle amplification (RCA), the Invader™ Assay, or oligonucleotide ligation assay (OLA). OLA may be used for revealing base polymorphisms. According to this method, two oligonucleotides are constructed that hybridize to adjacent sequences in the target nucleic acid, with the join sited at the position of the polymorphism. DNA ligase will covalently join the two oligonucleotides only if they are perfectly hybridized to one of the allele.

Therefore, useful nucleic acid molecules, in particular oligonucleotide probes or primers, according to the present invention include those which specifically hybridize the one of the allele of the polymorphism.

Oligonucleotide probes or primers may contain at least 10, 15, 20 or 30 nucleotides. Their length may be shorter than 400, 300, 200 or 100 nucleotides.

In some embodiments, the method of the invention is performed by a laboratory that will generate a test report. The test report will thus indicate whether the risk allele is present or absent, and preferably indicates whether the patient is heterozygous or homozygous for the risk allele. In some embodiments, the test result will include a probability score for developing liver fibrosis, which is derived from running a model that include the risk factor determined for the one or the two single nucleotide polymorphisms of the invention that are tested. For calculating the score, the risk factor determined for a single nucleotide polymorphism of the invention may be pondered by a coefficient depending on what is the contribution of said single nucleotide polymorphism in the determination of the risk in comparison with the other one single nucleotide polymorphism. Typically, the method for calculating the score is based on statistical studies performed on various cohorts of patients. The score may also include other various patient parameters (e.g., age, gender, weight, alcohol consumption of the subject, HCV genotype, HIV infection). The weight given to each parameter is based on its contribution relative to the other parameters in explaining the inter-individual variability of developing liver fibrosis. In some embodiments, the test report may be thus generated by a computer program for establishing such a score.

Another aspect of the invention then pertains to a method for the indication of the need for a preventive treatment with an anti-infective agent or anti-infective therapy in a subject, comprising the steps of determining in a sample isolated from said subject the presence of at least one genetic polymorphism selected from table 1 which indicates the subject for said preventive treatment or therapy.

A preventive treatment with an anti-infective agent or anti-infective therapy preferably involves the administration of an antibody against a HRSV protein, such as a prophylactic antibody targeting the G, F or SH envelope protein or a virus polymerase, and preferably is a treatment with palivizumab; or wherein said preventive treatment with an anti-infective agent or anti-infective therapy involves the administration of a vaccine against HRSV. In principle any treatment of HRSV may be used in this context. Some preferred approaches of HRSV treatment or prophylaxis is described in the above introduction.

A "subject" is preferably a human patient, such a human infant, for example child between 0 to 5 years of age, or a child between 0 and 3 years of age, or a child between 0 and 2 years of age, or a child between 0 and 1 year of age; and/or wherein the human patient is an immune suppressed patient such as the very young or elderly, or an immune compromised (adult) patient.

In some preferred embodiments the presence or absence of the polynucleotide is identified by amplifying or failing to amplify an amplification product from the sample, wherein the amplification product is preferably digested with a restriction enzyme before analysis and/or wherein the SNP is identified by hybridizing the nucleic acid sample with a primer label which is a detectable moiety.

Also provided is a computer program or a computer-readable media containing means for carrying out a method as defined in the present disclosure.

Another aspect pertains to a kit comprising reagents for detecting the identity of a genetic polymorphism containing nucleotide selected from table 1. Such a kit is preferably for use in any of the herein disclosed methods. In some embodiments the kit may comprise one or more nucleic acid primer pairs specific for the amplification of a region comprising at least one polymorphism selected from table 1.

Some of the herein disclosed genetic polymorphisms were surprisingly identified to be located in novel genes which are functionally associated with virus infection. Such genes may be necessary for viral infection or have an activity of virus inhibitors. Therefore, the present invention pertains in another aspect to a compound for use in the treatment of a HRSV infection, wherein the compound is selected from (i) an antagonist of poly(A) binding protein cytoplasmic 1 (PABPC1), protein activator of interferon induced protein kinase EIF2AK2 (PRKRA), arylsulfatase D (ARSD), "MLLT6, PHD finger containing" (MLLT6) or CTD small phosphatase 2 (CTDSP2); or (ii) an agonist of C-terminal binding protein 2 (CTBP2), RNA polymerase mitochondrial (POLRMT), or transmembrane protein 259 (TMEM259). The genes are denoted according to the nomenclature of the human gene names project: Gray K A, Yates B, Seal R L, Wright M W, Bruford E A. genenames.org: the HGNC resources in 2015. Nucleic Acids Res. 2015 January; 43 (Database issue):D1079-85. doi: 10.1093/nar/gku1071. PMID: 25361968; HGNC Database, HUGO Gene Nomenclature Committee (HGNC), EMBL Outstation-Hinxton, European Bioinformatics Institute, Wellcome Trust Genome Campus, Hinxton, Cambridgeshire, CB10 1SD, UK www.genenames.org.

An "antagonists" in context of the present invention are preferably compounds impairing the expression, stability and/or function of the references proteins or their mRNA or genes. Most preferably the antagonist is an antagonist of a mammalian homologue of the respective factors. As used herein, the term "antagonist" means a substance that affects a decrease in the amount or rate of protein expression or activity. Such a substance can act directly, for example, by binding to the candidate protein and decreasing the amount or rate of its expression or activity. An antagonist can also decrease the amount or rate of protein expression or activity, for example, by binding to the referenced factor in such a way as to reduce or prevent interaction of it with an interaction partner such as a receptor or ligand; or by binding to the referenced protein and modifying it, such as by removal or addition of a moiety; and by binding to it and reducing its stability. An antagonist can also act indirectly, for example, by binding to a regulatory molecule or gene region so as to modulate regulatory protein or gene region function and affect a decrease in the amount or rate of protein expression or activity.

An antagonist of the invention can be, for example, a naturally or non-naturally occurring macromolecule, such as a polypeptide, peptide, peptidomimetic, nucleic acid, carbohydrate or lipid. An antagonist further can be an antibody, or antigen-binding fragment thereof, such as a mono-clonal antibody, humanized antibody, chimeric antibody, minibody, bifunctional antibody, single chain antibody (scFv), variable region fragment (Fv or Fd), Fab or F(ab)2. An antagonist can also be polyclonal antibodies specific for the respective protein. An antagonist further can be a partially or completely synthetic derivative, analog or mimetic f a naturally occurring macromolecule, or a small organic or inorganic molecule.

An antagonist that is an antibody can be, for example, an antibody that binds to the protein and inhibits binding to its receptor, or alters the activity of a molecule that regulates expression or activity, such that the amount or rate of protein expression or activity is decreased. An antibody useful in a method of the invention can be a naturally occurring antibody, including a monoclonal or polyclonal antibodies or fragment thereof, or a non-naturally occurring antibody, including but not limited to a single chain antibody, chimeric antibody, bifunctional antibody, complementarity determining region-grafted (CDR-grafted) antibody and humanized antibody or an antigen-binding fragment thereof.

An antagonist that is a nucleic acid can be, for example, an anti-sense nucleotide sequence, an RNA molecule, or an aptamer sequence. An anti-sense nucleotide sequence can bind to a nucleotide sequence within a cell and modulate the level of expression of the candidates protein or modulate expression of another gene that controls the expression or activity of the candidate protein. Similarly, an RNA molecule, such as a catalytic ribozyme, can bind to and alter the expression of a gene, or other gene that controls the expression or activity of the candidate of the invention. An aptamer is a nucleic acid sequence that has a three dimensional structure capable of binding to a molecular target.

An antagonist that is a nucleic acid also can be a double-stranded RNA molecule for use in RNA interference methods. RNA interference (RNAi) is a process of sequence-specific gene silencing by post-transcriptional RNA degradation, which is initiated by double-stranded RNA (dsRNA) homologous in sequence to the silenced gene. A suitable double-stranded RNA (dsRNA) for RNAi contains sense and antisense strands of about 21 contiguous nucleotides corresponding to the gene to be targeted that form 19 RNA base pairs, leaving overhangs of two nucleotides at each 3' end (Elbashir et al., Nature 411:494-498 (2001); Bass, Nature 411:428-429 (2001); Zamore, Nat. Struct. Biol. 8:746-750 (2001)). dsRNAs of about 25-30 nucleotides have also been used successfully for RNAi (Karabinos et al., Proc. Natl. Acad. Sci. USA 98:7863-7868 (2001). dsRNA can be synthesized in vitro and introduced into a cell by methods known in the art. Preferred antisense interference constructs are siRNA and shRNA or any other RNA based inhibitor. Also included are constructs and methods that use CRISPR/Cas9 mediated genome editing to impair protein expression. Such methods and compounds are well known in the art and require the skilled artisan to simply design and elect an appropriate genetic target sequence, which is known for all the herein disclosed target genes.

In other aspects the invention pertains to agonists of proteins identified herein as inhibitory for viral infection. These factors are useful when targeted with agonistic compounds. As used herein, the term "agonist" means a substance that affects an increase in the amount or rate of expression or activity of such a fector. Such a substance can act directly, for example, by binding to a protein and increasing the amount or rate of expression or activity. An agonist can also increase the amount or rate of expression or activity, for example, by binding to a protein in such a way as to enhance or promote interaction of it with a ligand or receptor; activation may be affected by binding to a protein and modifying it, such as inducing a conformational change, or removal or addition of a moiety; and by binding to a protein and enhancing its stability. An agonist can also act indirectly, for example, by binding to a regulatory molecule or gene region so as to modulate regulatory protein or gene region function and affect an increase in the amount or rate of expression or activity.

An agonist can be, for example, a naturally or non-naturally occurring macromolecule, such as a polypeptide, peptide, peptidomimetic, nucleic acid, carbohydrate or lipid. An agonist further can be an antibody, or antigen-binding fragment thereof, such as a mono-clonal antibody, humanized antibody, chimeric antibody, minibody, bifunctional antibody, single chain antibody (scFv), variable region fragment (Fv or Fd), Fab or F(ab)2. An agonist can also be a polyclonal antibody specific for a protein disclosed as a HRSV inhibitor of the invention. An agonist further can be a partially or completely synthetic derivative, analog or mimetic of a naturally occurring macromolecule, or a small organic or inorganic molecule.

An antibody useful in a method of the invention can be a naturally occurring antibody, including monoclonal or polyclonal antibodies or fragments thereof, or a non-naturally occurring antibody, including but not limited to a single chain antibody, chimeric antibody, bifunctional antibody, complementarity determining region-grafted (CDR-grafted) antibody and humanized antibody or an antigen-binding fragment thereof.

Agonists in accordance with the present invention are also expression constructs expressing any of the HRSV inhibitory proteins or functional fragments thereof. The term "expression construct" means any double-stranded DNA or double-stranded RNA designed to transcribe an RNA, e.g., a construct that contains at least one promoter operably linked to a downstream gene or coding region of interest (e.g., a cDNA or genomic DNA fragment that encodes a protein, or any RNA of interest)—in particular a gene of a HRSV inhibitor as identified herein or a fragment thereof. Transfection or transformation of the expression construct into a recipient cell allows the cell to express RNA or protein encoded by the expression construct. An expression construct may be a genetically engineered plasmid, virus, or an artificial chromosome derived from, for example, a bacteriophage, adenovirus, retrovirus, poxvirus, or herpesvirus, or further embodiments described under "expression vector" below. An expression construct can be replicated in a living cell, or it can be made synthetically. For purposes of this application, the terms "expression construct", "expression vector", "vector", and "plasmid" are used interchangeably to demonstrate the application of the invention in a general, illustrative sense, and are not intended to limit the invention to a particular type of expression construct. Further, the term expression construct or vector is intended to also include instances wherein the cell utilized for the assay already endogenously comprises such DNA sequence.

In another aspect there is provided a method for identifying the association of a genetic variant and an infectious disease, the method comprising sequencing the whole exome of a study cohort of patients infected with the infectious disease, variant calling in the sequenced exo-mes using reference genome data for a predetermined subset of genes, and comparing allele frequencies of said variants in the study cohort compared to a reference cohort, and identifying genetic variants significantly associated with the infectious disease.

Preferably the genetic variant is a genetic polymorphism, preferably a single nucleotide polymorphism (SNP).

Preferably, the infectious disease is a virus disease, for example is HSRV.

In context of the invention the term "reference cohort" preferably pertains to a sub-cohort of the exome aggregation database (available on the world wide web at exac.broadinstitute.org/). When selecting a reference cohort, the person of skill should a select a group that closely matches the genetic background of the study cohort. For example, as in the present case, if the study cohort is of a certain age group or ethnicity, the reference cohort should, insofar possible, match these criteria as well.

In context of the invention the predetermined subset of genes are genes regulated by interferon.

Further included are the above method which further comprises the further steps of validating the identified associated genetic variants.

The present invention will now be further described in the following examples with reference to the accompanying figures and sequences, nevertheless, without being limited thereto. For the purposes of the present invention, all references as cited herein are incorporated by reference in their entireties. In the Figures:

FIG. 1: shows study cohort characteristics.

Figure 2:
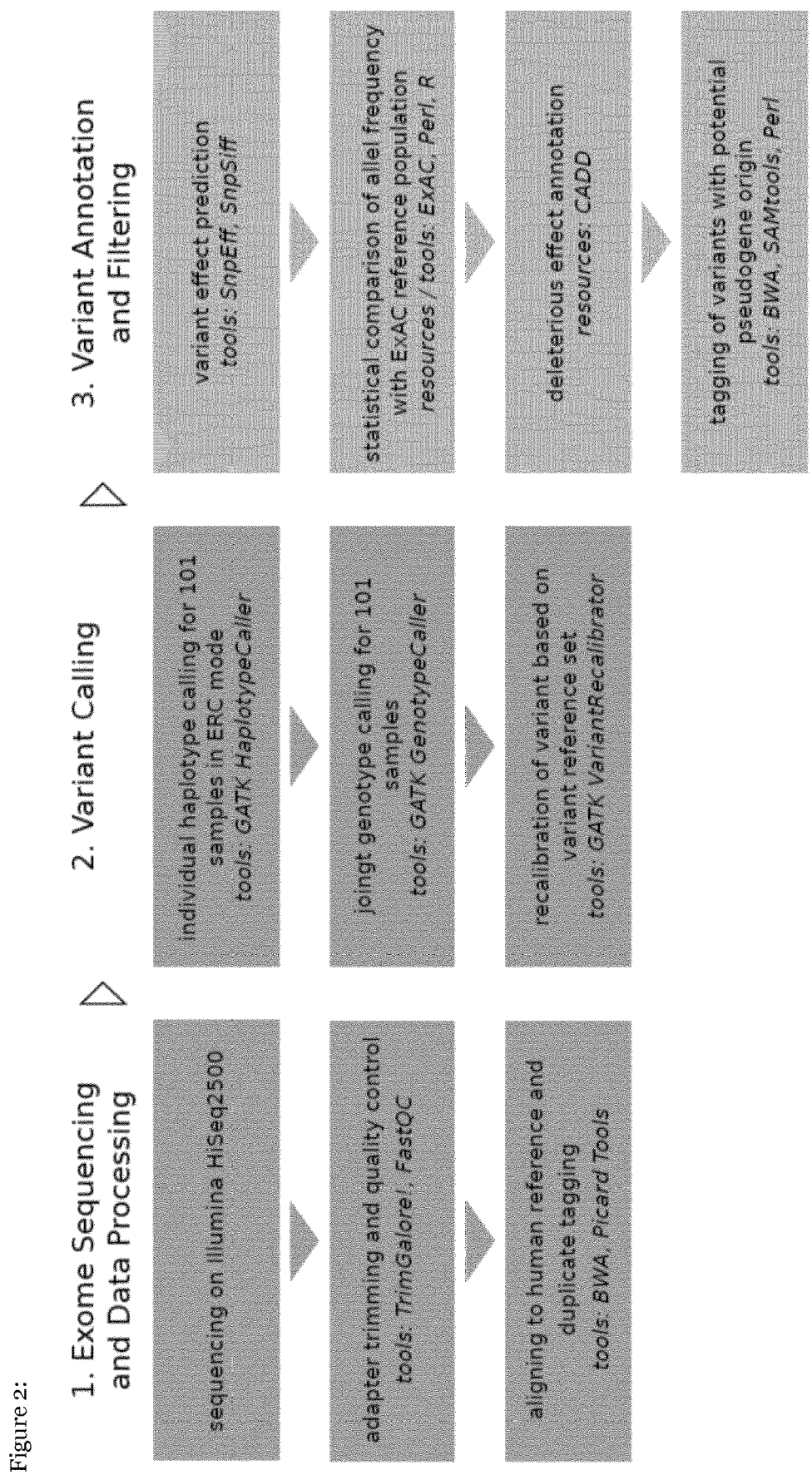
Figure 3:
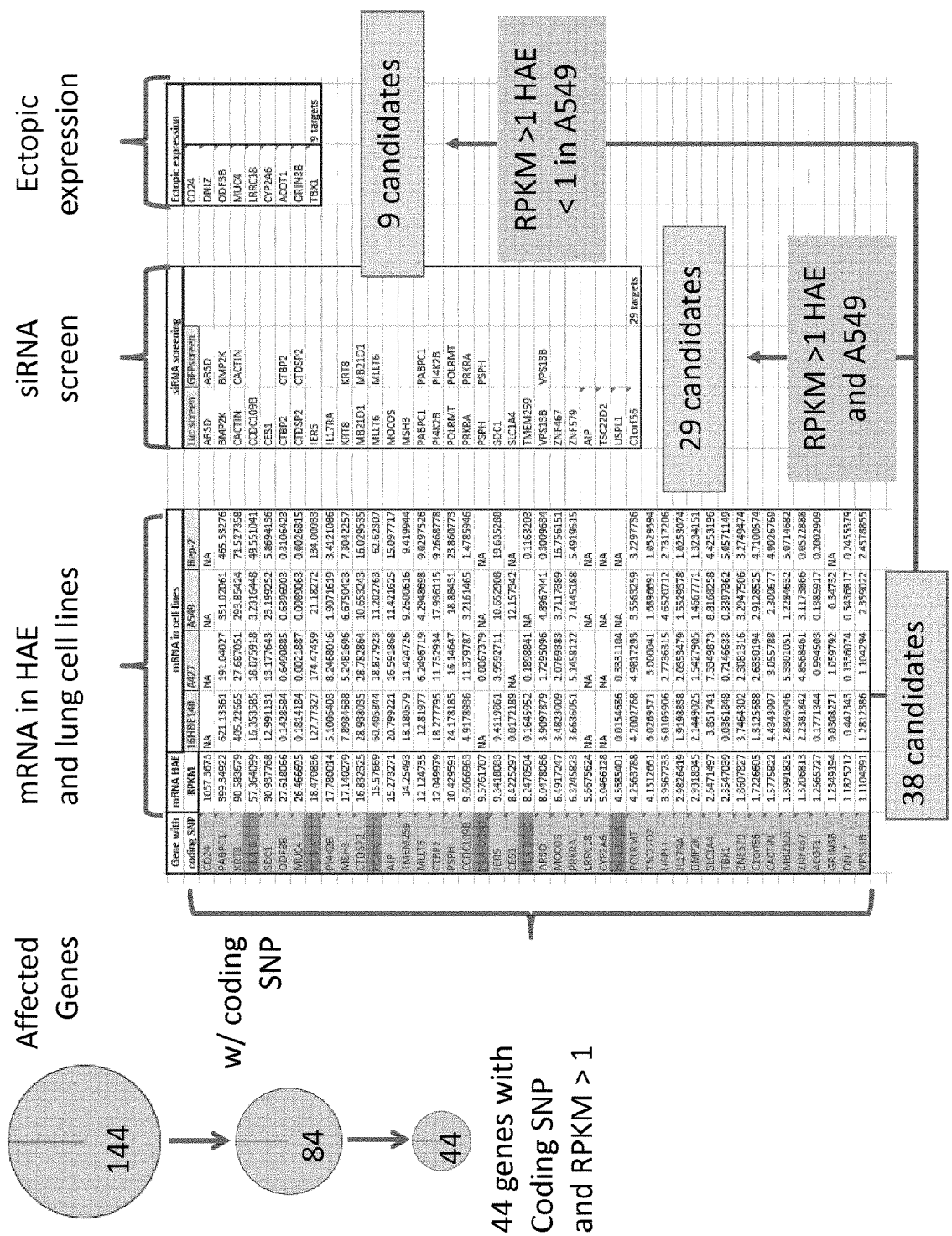

FIG. 2: shows the workflow of the exome sequencing and data processing, the variant calling and filtering process FIG. 3: shows the workflow of the sequencing and follow-up analysis.

Figure 4:
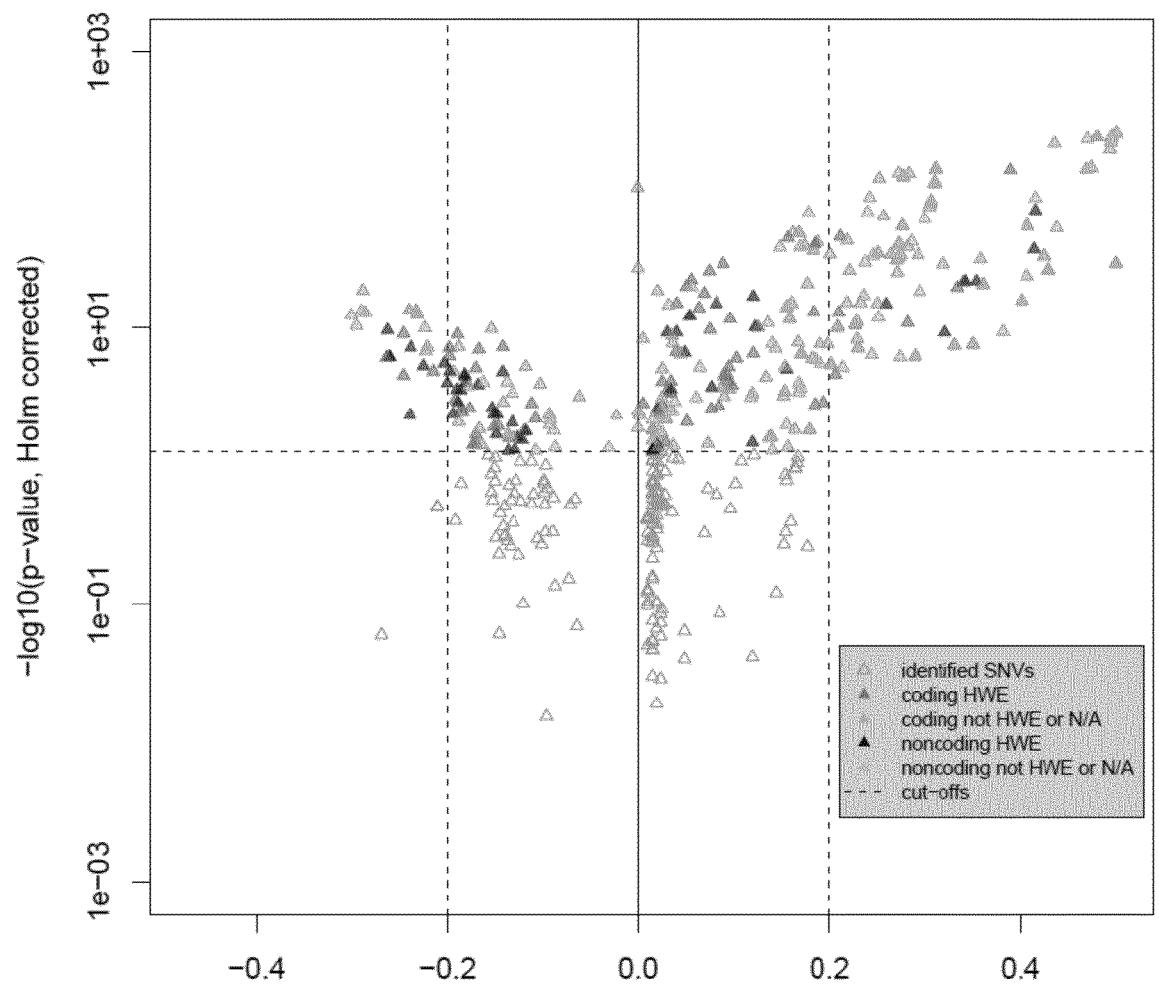

FIG. 4: shows a volcano plot of SNPs.

Figure 5:
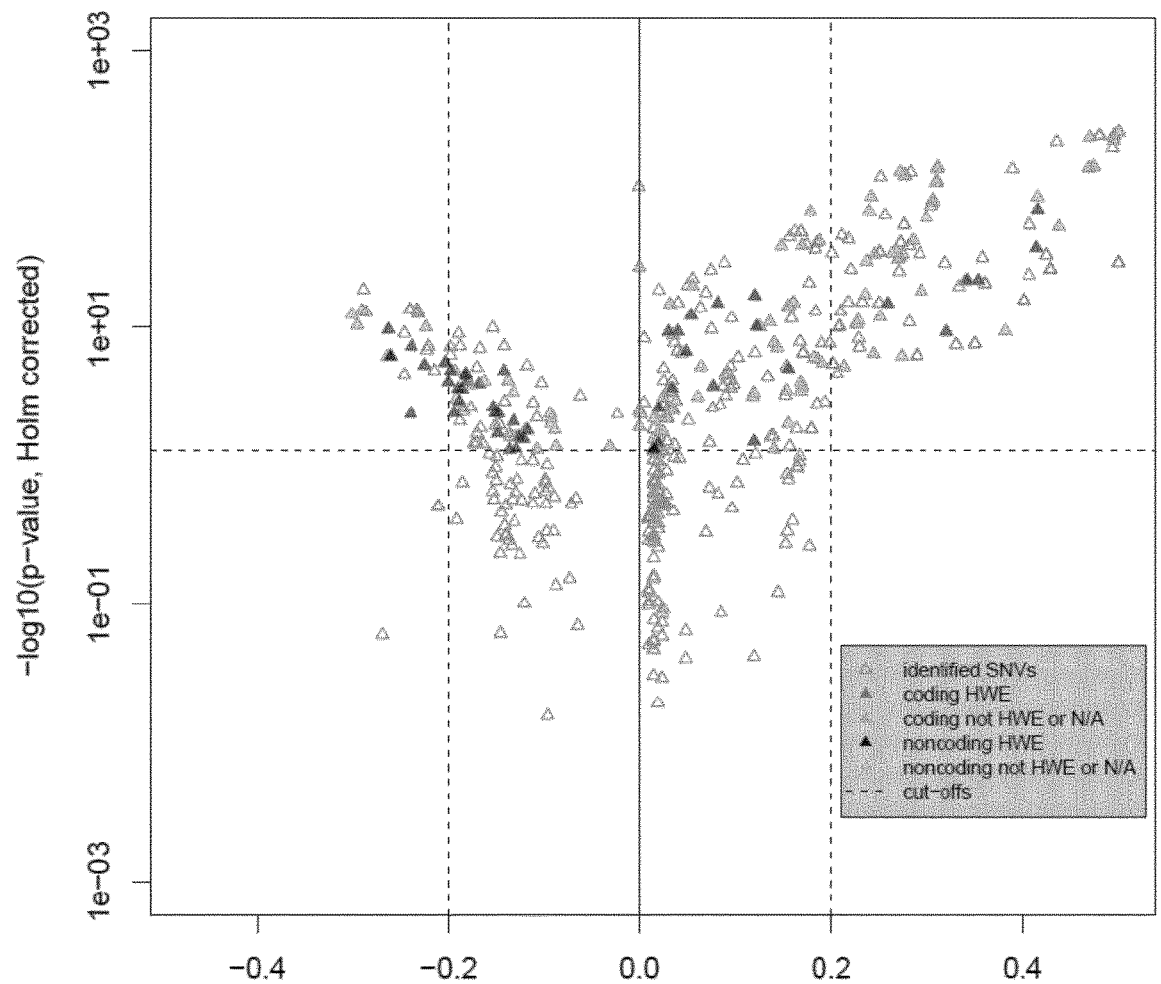

FIG. 5: shows a volcano plot of SNPs

Figure 6:
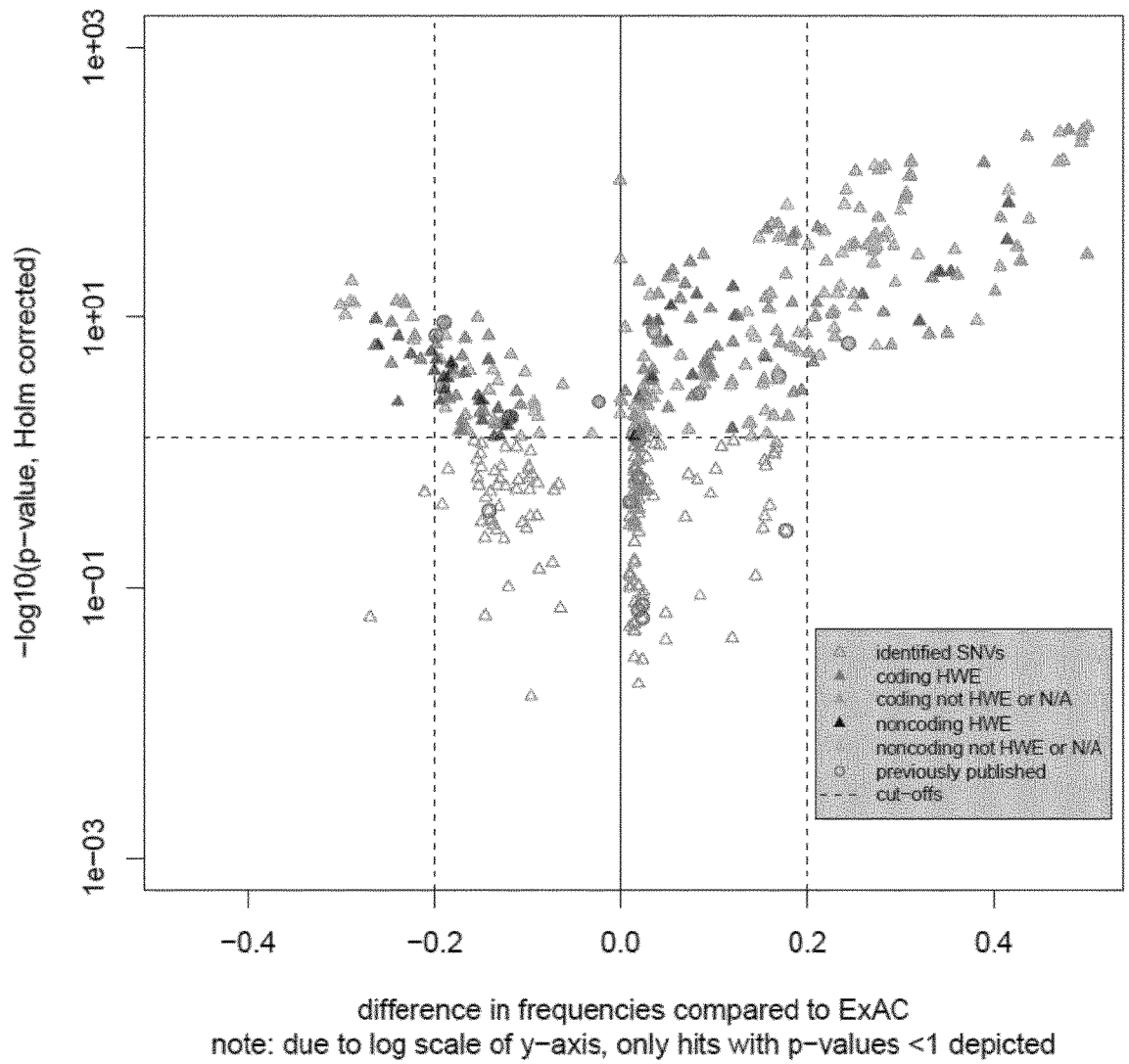

FIG. 6: shows a volcano plot of SNPs

Figure 7:
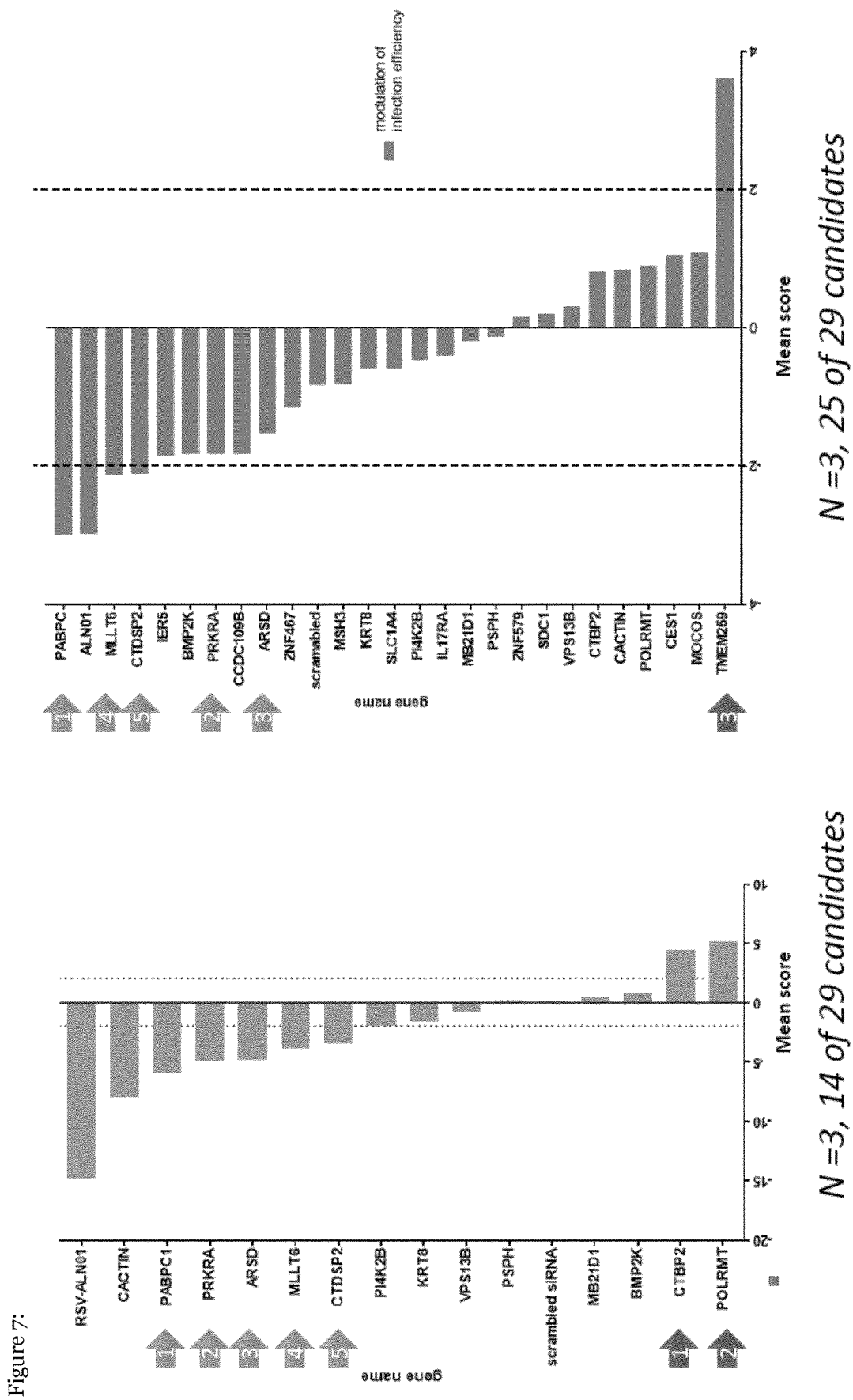

FIG. 7: shows the results of an siRNA screen. Left hand side shows the assay as published in Duprex et al. Right hand side shows Eleouet et al.

EXAMPLES

Example 1: Exome Sequencing and Variant Calling

The inclusion criteria for the study cohort were written consent of legal guardian, age (0-5 years) and Caucasian ethnicity. Patients suffered from severe RSV infection including acute respiratory infection, RSV in nasal swabs (PCR), need for hospitalization and hypoxemia. Exclusion criteria were prematurity (<36 SSW), bronchiopulmonary dysplasia, cardiac defect, or immunodeficiency. FIG. 1 shows study cohort characteristics.

The libraries were sequenced on Illumina HiSeq2500 using TruSeq SBS Kit v3-HS (200 cycles, paired end run) with an average of $12.5 \times 10^6$ reads per single exome (mean coverage: 50x). Quality of FASTQ files were determined before and after trimming by FastQC tool. Raw reads were further manipulated by TrimGalore! (default settings) in order to clip artificial illumina adapter sequences and to clip/remove bad quality sequence reads. Trimmed FASTQ files were aligned to human reference genome hg19 using BWA aligner tool followed by tagging duplicated reads (PCR products) with MarkDuplicates (Picard tools).

Variant calling was done for two patient subsets: 101 children with severe RSV infection and 70 children with very severe RSV infection (hypoxaemia). The Genome Analysis Toolkit (GATK) was used following its Best Practices guidelines. Specifically, HaplotypeCaller was run on individual samples in '-ERC GVCF' mode. Subsequently, joint variant calling was done using GenotypeCaller with the hg19 human genome build as reference. Recalibration of scores for single nucleotide variants and indels was done using VariantRecalibrator, and only variants that passed the 99.9% tranche threshold were considered for downstream analysis.

Variants of in total 5142 genes that are either directly regulated by interferons and/or participate in pathogen sensing and interferon signaling were analyzed. Interferon regulated genes (IRGs) were identified in (i) the Interferome database (cut off was at least 2-fold regulated, p-value<0.05; in total 4777 genes), and (ii) an in-house database of IRGs in primary human lung cells (Lauber C et al. Genes Immun. 2015 September; 16(6):414-21; 704 genes). Finally, the inventors used Ingenuity pathway analysis (IPA) to identify genes involved in pathogens sensing and IFN-signaling. To this end, the following operators were used in the gene and chemical lists: recombinant interferon, interferon alpha, interferon beta, interferon gamma, interferon signaling; in the pathways and tox lists: role of Jak1, Jak2 and Tyk2 in interferon signaling, role of PKR in interferon induction and antiviral response, activation of IRF by cytosolic pattern recognition receptors, role of pattern recognition receptors in recognition of bacteria and viruses; and in the disease and functions list: RSV. Of all tables of molecules, only those with human Entrez number were taken into account. In total 194 genes were extracted via IPA. In total 35 genes were identified by all three approaches as indicated in the Venn diagram and collectively a total number of 5142 genes was ultimately included in the analysis based on the selection criteria.

Variants found for these genes were annotated using SnpEff. Minor allele frequencies in the ExAC sub-cohort consisting of Americans and non-Finnish Europeans were added for each variant using a custom Perl script. The difference in minor allele frequency between our cohort and the ExAC sub-cohort (FREQ_DIFF_ExAC) was used for ranking of the variants. Heterozygosity and homozygosity counts in ExAC and our cohort were used to calculate the significance of association of a variant with severe RSV infection using the Fisher's exact test and the Cochran-Armitage test for trend (implemented in R). Deleterious effects of variants was assessed using Combined Annotation Dependent Depletion (CADD) scores. Genes were ranked according to different measures including the sum of FREQ_DIFF_ExAC values of all variants of a gene and the log-ratio of the sum of FREQ_DIFF_ExAC values of all non-synonymous variants to the sum of FREQ_DIFF_ExAC values of all silent variants of a gene.

Filtering of variants for those that display a significant shift in allele frequency revealed a total of 346 SNVs displaying a significant association. Of these 218 are coding SNVs and 128 are non-coding SNVs. In total these SNVs affected 144 genes. 84 genes were affected by coding SNVs, 87 by non-coding SNVs and 27 genes harboured both coding and non-coding SNVs Strategy for functional follow up of affected genes is provided in FIG. 3. In total 144 genes were affected by significantly associated SNVs. 84 genes carried coding SNVs and 44 of these genes express mRNA in primary human airway epithelial cells (HAE; RPKM>1). The six HLA genes meeting these inclusion criteria (affected by SNV and mRNA expressed in HAE at an RPKM>1) were excluded from functional follow up and are highlighted in red. The remaining 38 candidate genes were short listed for siRNA silencing in A549 cells (a human lung carcinoma cell line typically used for RSV infection studies) when the gene expressed an mRNA at an RPKM of >1 in these A549 cells (29 candidate genes fulfil this requirement). If the mRNA of the respective gene was not detected or was below an RPKM of 1, the gene was short listed for ectopic expression in A549 (9 candidate genes).

FIG. 4 shows an volcano plot highlighting all coding and non-coding SNPs with a Holm-corrected p value<0.05. Each SNV is plotted according to its p value (y-axis) and its frequency difference relative to the ExAC cohort (x-axis). The colour code indicates whether an identified SNV is coding (red/orange) or non-coding (dark/light blue). SNVs in Hardy Weinberg equilibrium (HWE) are plotted in dark colour, those not in HWE are plotted in light colour. FIG. 5 shows a volcano plot highlighting all non-coding SNVs. FIG. 6 shows a volcano plot highlighting all coding SNVs. FIG. 7 shows a volcano plot highlighting all SNVs. SNVs targeting genes that have previously been examined as antiviral effectors in vitro or in vivo are encircled.

Results of identified genetic polymorphisms are provided in the following table 1:

| CHROM | POS | GENE | SNP ID | REF | ALT | P_FISHER_holm |
|---|---|---|---|---|---|---|
| 17 | 67101718 | ABCA6 | rs7212506 | C | T | 2.76E-19 |
| 14 | 74008304 | ACOT1 | rs146335256 | G | A | 0.00438522 |
| 1 | 955597 | AGRN | rs115173026 | G | T | 0.00399997 |
| 5 | 1.78E+3008 | AGXT2L2 | rs116735771 | C | G | 5.38E-08 |
| 11 | 67257823 | AIP | rs641081 | C | A | 0.03166295 |
| 2 | 2.33E+3008 | ALPPL2 | rs75920311 | C | G | 1.80E-10 |
| 19 | 2114175 | AP3D1 | rs386421229 | T | C | 3.38E-05 |
| 12 | 12939892 | APOLD1 | rs4763876 | G | A | 0.024041547 |
| 23 | 2833628 | ARSD | rs373216270 | A | C | 1.93E-140 |
| 23 | 2833631 | ARSD | rs377542415 | A | G | 5.13E-144 |
| 23 | 2833638 | ARSD | rs370769167 | C | T | 9.36E-142 |
| 23 | 2833643 | ARSD | rs115332247 | C | A | 4.90E-141 |
| 23 | 2835863 | ARSD | rs78034736 | G | T | 1.84E-08 |
| 23 | 2835964 | ARSD | rs73632972 | G | A | 5.48E-84 |
| 23 | 2835985 | ARSD | rs748243474 | G | A | 6.83E-111 |
| 23 | 2835989 | ARSD | rs143238998 | A | C | 1.10E-114 |
| 23 | 2835993 | ARSD | rs755296450 | G | A | 8.09E-112 |
| 23 | 2835995 | ARSD | rs150899882 | C | A | 8.79E-112 |
| 23 | 2836037 | ARSD | rs211653 | G | C | 0.0341372 |
| 23 | 2836041 | ARSD | rs67272620 | A | T | 6.07E-76 |
| 23 | 2836047 | ARSD | rs67359049 | C | T | 2.13E-80 |
| 23 | 2836060 | ARSD | rs113318393 | G | A | 4.05E-62 |
| 23 | 2836084 | ARSD | rs73632973 | C | G | 6.01E-43 |
| 23 | 2836138 | ARSD | rs73632974 | G | A | 5.71E-18 |
| 23 | 2836181 | ARSD | rs73632975 | A | T | 1.04E-31 |
| 23 | 2836184 | ARSD | rs73632976 | C | T | 8.09E-33 |
| 23 | 2836211 | ARSD | rs73632977 | A | T | 2.29E-34 |
| 23 | 2836238 | ARSD | rs73632978 | G | A | 1.91E-39 |
| 1 | 1.97E+3008 | ASPM | rs16841081 | G | A | 0.024123288 |
| 14 | 92537379 | ATXN3 | rs12896583 | T | C,TGCTGCTGCTGCTGCTGCTGCTGC,TGC | 4.90E-14 |

-continued

| CHROM | POS | GENE | SNP ID | REF | ALT | P_FISHER_holm |
|---|---|---|---|---|---|---|
| | | | | | TGCTGCTGCTGCTG CTGC, TGCTGCTGCT GCTGCTGCTGCTGC TGC, TGCTGCTGCTG CTGC | |
| 14 | 92537379 | ATXN3 | rs12896583 | T | C, TGCTGCTGCTGCT GCTGCTGCTGC, TGC TGCTGCTGCTGCTG CTGC, TGCTGCTGCT GCTGCTGCTGCTGC TGC, TGCTGCTGCTG CTGC | 4.90E-14 |
| 14 | 92537379 | ATXN3 | rs12896583 | T | C, TGCTGCTGCTGCT GCTGCTGCTGC, TGC TGCTGCTGCTGCTG CTGC, TGCTGCTGCT GCTGCTGCTGCTGC TGC, TGCTGCTGCTG CTGC | 4.90E-14 |
| 14 | 92537379 | ATXN3 | rs12896583 | T | C, TGCTGCTGCTGCT GCTGCTGCTGC, TGC TGCTGCTGCTGCTG CTGC, TGCTGCTGCT GCTGCTGCTGCTGC TGC, TGCTGCTGCTG CTGC | 4.90E-14 |
| 14 | 92537379 | ATXN3 | rs12896583 | T | C, TGCTGCTGCTGCT GCTGCTGCTGC, TGC TGCTGCTGCTGCTG CTGC, TGCTGCTGCT GCTGCTGCTGCTGC TGC, TGCTGCTGCTG CTGC | 4.90E-14 |
| 14 | 92537387 | ATXN3 | rs12896588 | T | G, TGC | 3.95E-14 |
| 14 | 92537387 | ATXN3 | rs12896588 | T | G, TGC | 3.95E-14 |
| 14 | 92537388 | ATXN3 | rs12896589 | T | C, TGCTGCTGCTGC, T GCTGCTGCTGCTGC TGCTGC, TGCTGCTG CTGCTGC | 2.36E-13 |
| 14 | 92537388 | ATXN3 | rs12896589 | T | C, TGCTGCTGCTGC, T GCTGCTGCTGCTGC TGCTGC, TGCTGCTG CTGCTGC | 2.36E-13 |
| 14 | 92537388 | ATXN3 | rs12896589 | T | C, TGCTGCTGCTGC, T GCTGCTGCTGCTGC TGCTGC, TGCTGCTG CTGCTGC | 2.36E-13 |
| 14 | 92537388 | ATXN3 | rs12896589 | T | C, TGCTGCTGCTGC, T GCTGCTGCTGCTGC TGCTGC, TGCTGCTG CTGCTGC | 2.36E-13 |
| 4 | 79697870 | BMP2K | rs149914551 | C | A | 5.21E-06 |
| 1 | 2.47E+3008 | C1orf229 | rs73135916 | A | G | 4.61E-09 |
| 1 | 2.47E+3008 | C1orf229 | rs141557009 | C | G | 0.004110016 |
| 1 | 1.51E+3008 | C1orf56 | rs74856367 | C | T | 0.014465325 |
| 19 | 3613346 | CACTIN | rs2074789 | G | A | 0.001568078 |
| 22 | 37900243 | CARD10 | rs3817802 | G | A | 1.49E-05 |
| 4 | 1.11E+3008 | CCDC109B | rs4698744 | T | A | 0.000889267 |
| 24 | 21154426 | CD24 | rs52812045 | G | A | 5.46E-16 |

-continued

| CHROM | POS | GENE | SNP ID | REF | ALT | P_FISHER_holm |
|---|---|---|---|---|---|---|
| 24 | 21154466 | CD24 | rs10465460 | T | A | 1.75E-24 |
| 16 | 55866934 | CES1 | 0 | A | C | 1.55E-08 |
| 1 | 1.97E+3008 | CFHR1 | rs111236855 | T | C | 0.016445559 |
| 1 | 1.97E+3008 | CFHR1 | rs3201739 | A | G | 2.83E-06 |
| 19 | 17666636 | COLGALT1 | rs7259723 | C | T | 1.18E-12 |
| 1 | 2.08E+3008 | CR1 | rs17047661 | A | G | 0.03825975 |
| 1 | 1.97E+3008 | CRB1 | rs3902057 | A | G | 0.04979672 |
| 10 | 1.27E+3008 | CTBP2 | rs77603788 | C | T | 2.24E-216 |
| 10 | 1.27E+3008 | CTBP2 | 0 | G | A | 5.14E-10 |
| 12 | 58217708 | CTDSP2 | rs12822897 | G | A | 1.13E-17 |
| 12 | 58217738 | CTDSP2 | rs192597051 | G | A | 2.42E-233 |
| 12 | 58220809 | CTDSP2 | rs78691025 | G | C,T | 4.29E-255 |
| 12 | 58220816 | CTDSP2 | rs76940645 | A | G | 4.18E-255 |
| 12 | 58220831 | CTDSP2 | 0 | C | G,A | 5.10E-239 |
| 12 | 58220831 | CTDSP2 | 0 | C | G,A | 5.10E-239 |
| 12 | 58220831 | CTDSP2 | 0 | C | G,A | 5.10E-239 |
| 12 | 58220831 | CTDSP2 | 0 | C | G,A | 5.10E-239 |
| 6 | 1.32E+3008 | CTGF | rs6934749 | T | G | 0.01234688 |
| 7 | 1.02E+3008 | CUX1 | 0 | G | A | 5.22E-10 |
| 19 | 41355820 | CYP2A6 | rs199702575 | A | G | 1.06E-15 |
| 19 | 41355828 | CYP2A6 | rs200582200 | C | T | 6.46E-16 |
| 19 | 41355849 | CYP2A6 | rs2302990 | A | G | 2.79E-88 |
| 4 | 5021149 | CYTL1 | rs35263598 | G | A | 0.00231564 |
| 8 | 1616640 | DLGAP2 | rs4565482 | G | A | 0.019198865 |
| 9 | 1.39E+3008 | DNLZ | rs3812552 | C | G | 0.001242585 |
| 2 | 2.26E+3008 | DOCK10 | rs12328236 | G | A | 0.008104992 |
| 2 | 2.26E+3008 | DOCK10 | rs7577271 | A | G | 0.023850506 |
| 8 | 86089787 | E2F5 | rs12926 | C | G | 0.00986827 |
| 23 | 65824986 | EDA2R | rs1385699 | C | T | 0.022914944 |
| 1 | 16384986 | FAM131C | rs28496958 | G | T | 3.97E-11 |
| 1 | 16384998 | FAM131C | rs1807285 | G | C | 5.43E-14 |
| 1 | 16384999 | FAM131C | rs1807284 | G | A | 1.17E-13 |
| 1 | 16385042 | FAM131C | rs77667563 | G | A | 1.46E-07 |
| 20 | 54934067 | FAM210B | rs190100022 | C | T | 0.000400664 |
| 1 | 1.52E+3008 | FLG | rs562496957 | A | C | 1.08E-20 |
| 9 | 71650752 | FXN | rs2481598 | A | G | 0.003145488 |
| 22 | 24640612 | GGT5 | rs79754578 | C | A | 4.77E-23 |
| 6 | 39016636 | GLP1R | rs10305420 | C | T | 0.001275674 |

-continued

| CHROM | POS | GENE | SNP ID | REF | ALT | P_FISHER_holm |
|---|---|---|---|---|---|---|
| 2 | 2.41E+3008 | GPC1 | rs2228327 | C | T | 0.000257881 |
| 1 | 1.68E+3008 | GPR161 | rs73030230 | T | A | 0.019610616 |
| 19 | 48945880 | GRIN2D | rs62130268 | T | C | 0.000723696 |
| 19 | 1009585 | GRIN3B | rs10401454 | C | G | 0.03606168 |
| 17 | 3627619 | GSG2 | rs1185511 | C | T | 0.001143261 |
| 4 | 1.45E+3008 | GYPA | rs4867 | A | G | 0.003007746 |
| 4 | 1.45E+3008 | GYPA | rs7682260 | A | G | 5.44E-26 |
| 9 | 99212909 | HABP4 | rs754559 | G | C | 4.17E-13 |
| 20 | 62196033 | HELZ2 | rs3810487 | C | T | 0.011355544 |
| 7 | 27702390 | HIBADH | rs11550134 | C | A | 1.57E-05 |
| 7 | 75176300 | HIP1 | 0 | T | C | 9.24E-05 |
| 6 | 29911056 | HLA-A | rs1071743 | A | C,G | 3.43E-06 |
| 6 | 29911056 | HLA-A | rs1071743 | A | C,G | 3.43E-06 |
| 6 | 29911063 | HLA-A | rs199474485 | T | G | 2.92E-11 |
| 6 | 31324194 | HLA-B | rs3179865 | G | A | 6.12E-06 |
| 6 | 31324201 | HLA-B | rs1071652 | C | G,T,A | 2.88E-07 |
| 6 | 31324201 | HLA-B | rs1071652 | C | G,T,A | 2.88E-07 |
| 6 | 31324201 | HLA-B | rs1071652 | C | G,T,A | 2.88E-07 |
| 6 | 31324206 | HLA-B | rs1131235 | G | A | 7.13E-08 |
| 6 | 31324586 | HLA-B | rs1050556 | C | T | 1.60E-22 |
| 6 | 31324595 | HLA-B | rs1050543 | C | G | 1.28E-15 |
| 6 | 31324599 | HLA-B | rs1050538 | T | G | 0.00248631 |
| 6 | 31324603 | HLA-B | rs200186034 | CT | C,TT | 9.49E-34 |
| 6 | 31324603 | HLA-B | rs200186034 | CT | C,TT | 9.49E-34 |
| 6 | 31324604 | HLA-B | rs9266179 | T | C | 9.50E-06 |
| 6 | 31324864 | HLA-B | rs151341076 | G | A | 6.89E-11 |
| 6 | 31324887 | HLA-B | rs1131165 | G | C | 3.60E-22 |
| 6 | 31324888 | HLA-B | rs1131163 | G | T | 1.44E-22 |
| 6 | 31324892 | HLA-B | rs1131159 | G | C | 1.21E-11 |
| 6 | 31324895 | HLA-B | rs1131156 | G | C | 2.42E-20 |
| 6 | 31324911 | HLA-B | rs1050462 | C | G | 1.10E-13 |
| 6 | 31324925 | HLA-B | rs1050458 | A | G | 0.002431296 |
| 6 | 31324931 | HLA-B | rs9266206 | A | C | 0.003393693 |
| 6 | 31238897 | HLA-C | rs150127748 | C | G | 0.001719854 |
| 6 | 31238931 | HLA-C | rs697743 | G | A,GTC | 0.000201241 |
| 6 | 32609213 | HLA-DQA1 | 0 | G | A | 3.85E-05 |
| 6 | 32609227 | HLA-DQA1 | 0 | A | C | 5.87E-06 |
| 6 | 32609228 | HLA-DQA1 | 0 | G | A | 0.00062163 |
| 6 | 32609231 | HLA-DQA1 | 0 | A | G | 1.23E-08 |

-continued

| CHROM | POS | GENE | SNP ID | REF | ALT | P_FISHER_holm |
|---|---|---|---|---|---|---|
| 6 | 32609233 | HLA-DQA1 | 0 | T | C | 3.21E-05 |
| 6 | 32609236 | HLA-DQA1 | rs4193 | G | A | 2.37E-05 |
| 6 | 32609271 | HLA-DQA1 | 0 | G | C | 2.39E-32 |
| 6 | 32609278 | HLA-DQA1 | 0 | G | A,C | 2.26E-41 |
| 6 | 32609278 | HLA-DQA1 | 0 | G | A,C | 2.26E-41 |
| 6 | 32609279 | HLA-DQA1 | rs777760029 | C | T,CCT | 1.98E-55 |
| 6 | 32609279 | HLA-DQA1 | rs777760029 | C | T,CCT | 1.98E-55 |
| 6 | 32609286 | HLA-DQA1 | 0 | C | T | 2.07E-71 |
| 6 | 32609299 | HLA-DQA1 | rs1064944 | A | C,G | 1.94E-55 |
| 6 | 32609299 | HLA-DQA1 | rs1064944 | A | C,G | 1.94E-55 |
| 6 | 32609312 | HLA-DQA1 | 0 | A | C | 2.65E-141 |
| 6 | 32712977 | HLA-DQA2 | 0 | C | T | 1.16E-14 |
| 6 | 32712979 | HLA-DQA2 | 0 | C | T | 4.61E-10 |
| 6 | 32713061 | HLA-DQA2 | 0 | C | A | 8.08E-05 |
| 6 | 32713070 | HLA-DQA2 | 0 | A | C | 1.55E-18 |
| 6 | 32713075 | HLA-DQA2 | 0 | T | C | 6.65E-13 |
| 6 | 32713076 | HLA-DQA2 | 0 | A | C | 6.67E-13 |
| 6 | 32713080 | HLA-DQA2 | 0 | A | G | 1.79E-07 |
| 6 | 32713086 | HLA-DQA2 | 0 | T | G | 0.001465985 |
| 6 | 32713090 | HLA-DQA2 | 0 | T | A | 0.000334396 |
| 6 | 32713598 | HLA-DQA2 | 0 | T | C | 9.60E-27 |
| 6 | 32713602 | HLA-DQA2 | 0 | T | C | 1.10E-30 |
| 6 | 32713608 | HLA-DQA2 | 0 | G | A | 2.18E-69 |
| 6 | 32713828 | HLA-DQA2 | 0 | G | A | 0.00766446 |
| 6 | 32714117 | HLA-DQA2 | 0 | C | G | 1.24E-42 |
| 6 | 32714125 | HLA-DQA2 | 0 | A | G | 7.45E-35 |
| 6 | 32714168 | HLA-DQA2 | 0 | A | G | 9.93E-05 |
| 6 | 32628022 | HLA-DQB1 | rs1140347 | A | G | 6.00E-38 |
| 6 | 32632592 | HLA-DQB1 | rs1140319 | C | G | 5.45E-11 |
| 6 | 32632593 | HLA-DQB1 | rs1140318 | C | T | 9.97E-11 |
| 6 | 32632599 | HLA-DQB1 | rs9274379 | A | G | 2.18E-08 |
| 6 | 32632605 | HLA-DQB1 | rs1140317 | C | A | 0.014274008 |
| 6 | 32632628 | HLA-DQB1 | rs1130392 | G | C | 0.0239598 |
| 6 | 32632635 | HLA-DQB1 | rs9274384 | A | C | 0.000588498 |
| 6 | 32632637 | HLA-DQB1 | rs1130387 | T | G | 0.000323353 |
| 6 | 32632749 | HLA-DQB1 | 0 | A | T,C | 0.000184938 |
| 6 | 32632749 | HLA-DQB1 | 0 | A | T,C | 0.000184938 |
| 6 | 32632753 | HLA-DQB1 | rs9274402 | C | T | 0.000181904 |

-continued

| CHROM | POS | GENE | SNP ID | REF | ALT | P_FISHER_holm |
|---|---|---|---|---|---|---|
| 6 | 32632769 | HLA-DQB1 | 0 | T | C | 5.90E-06 |
| 6 | 32632775 | HLA-DQB1 | rs9274405 | G | C | 7.28E-05 |
| 6 | 32546879 | HLA-DRB1 | 0 | A | G | 1.22E-46 |
| 6 | 32548032 | HLA-DRB1 | 0 | T | G | 1.52E-09 |
| 6 | 32549340 | HLA-DRB1 | 0 | C | G | 8.69E-16 |
| 6 | 32549344 | HLA-DRB1 | 0 | T | C | 0.03193712 |
| 6 | 32551928 | HLA-DRB1 | 0 | G | A | 9.14E-07 |
| 6 | 32551935 | HLA-DRB1 | 0 | G | A | 8.44E-05 |
| 6 | 32552056 | HLA-DRB1 | 0 | A | G | 8.10E-44 |
| 6 | 32552057 | HLA-DRB1 | 0 | C | G | 7.61E-11 |
| 6 | 32552080 | HLA-DRB1 | 0 | T | C,A | 2.21E-12 |
| 6 | 32552080 | HLA-DRB1 | 0 | T | C,A | 2.21E-12 |
| 6 | 32552081 | HLA-DRB1 | 0 | A | G | 5.31E-65 |
| 6 | 32552085 | HLA-DRB1 | 0 | G | C,T | 6.43E-08 |
| 6 | 32552085 | HLA-DRB1 | 0 | G | C,T | 6.43E-08 |
| 6 | 32552091 | HLA-DRB1 | 0 | G | C,T | 0.000231916 |
| 6 | 32552091 | HLA-DRB1 | 0 | G | C,T | 0.000231916 |
| 6 | 32552095 | HLA-DRB1 | 0 | C | T | 7.87E-30 |
| 6 | 32552127 | HLA-DRB1 | 0 | C | T | 2.26E-12 |
| 6 | 32552130 | HLA-DRB1 | 0 | C | A,CCTG | 2.26E-08 |
| 6 | 32552130 | HLA-DRB1 | 0 | C | A,CCTG | 2.26E-08 |
| 6 | 32552131 | HLA-DRB1 | 0 | C | G,A | 3.08E-08 |
| 6 | 32552131 | HLA-DRB1 | 0 | C | G,A | 3.08E-08 |
| 6 | 32552132 | HLA-DRB1 | 0 | TCTTAG | ACTTAG,CCTTAG,T,TATACTTAG | 6.33E-30 |
| 6 | 32552132 | HLA-DRB1 | 0 | TCTTAG | ACTTAG,CCTTAG,T,TATACTTAG | 6.33E-30 |
| 6 | 32552132 | HLA-DRB1 | 0 | TCTTAG | ACTTAG,CCTTAG,T,TATACTTAG | 6.33E-30 |
| 6 | 32552134 | HLA-DRB1 | 0 | T | G | 0.04183648 |
| 6 | 32552137 | HLA-DRB1 | rs769779152 | G | GA,A,C | 6.56E-27 |
| 6 | 32552137 | HLA-DRB1 | rs769779152 | G | GA,A,C | 6.56E-27 |
| 6 | 32552137 | HLA-DRB1 | rs769779152 | G | GA,A,C | 6.56E-27 |
| 6 | 32552138 | HLA-DRB1 | rs749085224 | G | GTA,C | 5.68E-07 |
| 6 | 32552138 | HLA-DRB1 | rs749085224 | G | GTA,C | 5.68E-07 |
| 6 | 32552140 | HLA-DRB1 | rs768883657 | TG | T,AG | 1.97E-21 |
| 6 | 32552140 | HLA-DRB1 | rs768883657 | TG | T,AG | 1.97E-21 |
| 6 | 32552144 | HLA-DRB1 | rs773489989 | AC | A,CC | 1.35E-16 |
| 6 | 32552144 | HLA-DRB1 | rs773489989 | AC | A,CC | 1.35E-16 |
| 6 | 32552147 | HLA-DRB1 | 0 | G | A | 3.68E-19 |

-continued

| CHROM | POS | GENE | SNP ID | REF | ALT | P_FISHER_holm |
|---|---|---|---|---|---|---|
| 6 | 32557436 | HLA-DRB1 | rs201614260 | C | G | 8.89E-07 |
| 6 | 32557446 | HLA-DRB1 | rs148093782 | G | C | 2.41E-05 |
| 6 | 32557461 | HLA-DRB1 | rs35053532 | A | G | 1.91E-49 |
| 6 | 32557465 | HLA-DRB1 | rs34187469 | G | A | 5.17E-69 |
| 6 | 32557477 | HLA-DRB1 | rs150644773 | G | A | 3.07E-34 |
| 6 | 32557480 | HLA-DRB1 | 0 | C | G | 8.57E-16 |
| 6 | 32557486 | HLA-DRB1 | rs201540428 | T | A | 1.83E-35 |
| 6 | 32557487 | HLA-DRB1 | rs34396110 | G | A | 2.39E-39 |
| 6 | 32557489 | HLA-DRB1 | rs199514452 | A | T | 1.79E-35 |
| 6 | 32557502 | HLA-DRB1 | 0 | G | GC,C | 1.37E-20 |
| 6 | 32557503 | HLA-DRB1 | rs201726340 | A | G | 0.000136863 |
| 5 | 1.63E+3008 | HMMR | rs380101 | G | A | 7.31E-28 |
| 1 | 1.81E+3008 | IER5 | rs1361365 | A | G | 0.004357798 |
| 9 | 21239578 | IFNA14 | rs141933410 | C | T | 2.18E-07 |
| 17 | 38600092 | IGFBP4 | rs598892 | G | A | 8.97E-11 |
| 22 | 17590180 | IL17RA | rs41323645 | G | A | 7.47E-10 |
| 5 | 1878212 | IRX4 | rs2279589 | G | A | 0.000130513 |
| 3 | 52852138 | ITIH4 | rs2245536 | A | G | 0.006672182 |
| 3 | 52853480 | ITIH4 | rs2276814 | T | A | 0.005955984 |
| 1 | 1.75E+3008 | KIAA0040 | rs2072035 | C | T | 3.58E-07 |
| 1 | 39879366 | KIAA0754 | rs604316 | T | C | 3.80E-39 |
| 19 | 55286854 | KIR2DL1 | 0 | A | G | 4.76E-132 |
| 19 | 55294969 | KIR2DL1 | 0 | A | G | 1.01E-132 |
| 19 | 55250036 | KIR2DL3 | 0 | T | C | 3.61E-139 |
| 19 | 55258830 | KIR2DL3 | 0 | C | T | 8.17E-124 |
| 19 | 55258831 | KIR2DL3 | 0 | G | A | 1.66E-126 |
| 19 | 55317436 | KIR2DL4 | 0 | G | A | 2.79E-49 |
| 19 | 55317456 | KIR2DL4 | 0 | G | A | 0.014356155 |
| 19 | 55317490 | KIR2DL4 | 0 | A | G | 4.50E-37 |
| 19 | 55317524 | KIR2DL4 | 0 | G | A | 6.43E-07 |
| 19 | 55324635 | KIR2DL4 | 0 | T | C | 3.84E-145 |
| 19 | 55325455 | KIR2DL4 | 0 | G | A | 2.40E-41 |
| 12 | 53298675 | KRT8 | rs771489011 | A | C | 1.63E-26 |
| 17 | 39340910 | KRTAP4-1 | rs2320231 | T | C | 4.16E-09 |
| 17 | 18390993 | LGALS9C | rs3907320 | C | T | 0.04183648 |
| 19 | 54745496 | LILRA6 | rs61734495 | C | T | 0.03358782 |
| 19 | 54726816 | LILRB3 | rs80332440 | A | T | 0.000353715 |
| 19 | 55317436 | LOC100287534 | 0 | G | A | 2.79E-49 |
| 19 | 55317456 | LOC100287534 | 0 | G | A | 0.014356155 |

| CHROM | POS | GENE | SNP ID | REF | ALT | P_FISHER_holm |
|---|---|---|---|---|---|---|
| 19 | 55317490 | LOC100287534 | 0 | A | G | 4.50E-37 |
| 19 | 55317524 | LOC100287534 | 0 | G | A | 6.43E-07 |
| 19 | 55324635 | LOC100287534 | 0 | T | C | 3.84E-145 |
| 19 | 55325455 | LOC100287534 | 0 | G | A | 2.40E-41 |
| 2 | 1.01E+3008 | LONRF2 | rs74177696 | C | G | 6.75E-12 |
| 10 | 50121515 | LRRC18 | rs61730452 | G | A | 0.013723884 |
| 14 | 24785784 | LTB4R | rs1046584 | C | T | 0.000265058 |
| 23 | 1.41E+3008 | MAGEC1 | rs176040 | C | T | 4.60E-08 |
| 23 | 1.41E+3008 | MAGEC1 | rs148942485 | T | C | 0.000638138 |
| 23 | 1.41E+3008 | MAGEC1 | rs77648555 | T | C | 1.18E-10 |
| 23 | 1.41E+3008 | MAGEC1 | rs57227275 | T | C | 3.22E-07 |
| 6 | 74161762 | MB21D1 | rs35629782 | G | T | 9.36E-10 |
| 1 | 1.51E+3008 | MCL1 | rs75018646 | T | C | 0.04788132 |
| 6 | 30673340 | MDC1 | rs144700924 | A | G | 0.000395152 |
| 6 | 30673351 | MDC1 | rs149535951 | C | G | 0.000238265 |
| 6 | 30673359 | MDC1 | rs143258964 | T | G | 7.69E-05 |
| 15 | 1E+3008 | MEF2A | rs325407 | G | A | 0.00303523 |
| 17 | 36861983 | MLLT6 | rs17855918 | T | C | 0.00141082 |
| 18 | 33767568 | MOCOS | rs113873219 | C | A | 0.01047394 |
| 5 | 79950781 | MSH3 | rs1650697 | A | G | 9.76E-14 |
| 11 | 1075850 | MUC2 | rs11825969 | G | A | 0.000147359 |
| 11 | 1075920 | MUC2 | rs11825977 | G | A | 5.05E-08 |
| 11 | 1085791 | MUC2 | rs41527753 | C | T | 0.002439486 |
| 3 | 1.96E+3008 | MUC4 | rs6805660 | T | C | 0.024618078 |
| 9 | 1.29E+3008 | MVB12B | rs76544515 | G | A | 8.66E-05 |
| 19 | 46394187 | MYPOP | rs62111265 | C | T | 9.90E-05 |
| 18 | 77170569 | NFATC1 | rs2230113 | G | A | 0.04897492 |
| 22 | 50970068 | ODF3B | rs141953471 | C | T | 9.37E-08 |
| 11 | 5474949 | OR51I2 | rs80243568 | A | G | 0.03523712 |
| 1 | 40235448 | OXCT2 | rs150795467 | C | T | 2.74E-07 |
| 8 | 1.02E+3008 | PABPC1 | rs139094790 | G | A | 5.85E-16 |
| 23 | 48690416 | PCSK1N | rs6520383 | G | T | 0.048153 |
| 8 | 22436681 | PDLIM2 | rs11545016 | C | T | 7.09E-07 |
| 4 | 25235801 | PI4K2B | rs10021593 | G | A | 6.24E-08 |
| 4 | 25236017 | PI4K2B | rs313549 | T | C | 0.00438522 |
| 1 | 2418625 | PLCH2 | rs7512269 | C | T | 0.04650711 |
| 3 | 1.29E+3008 | PLXND1 | rs1110168 | C | G | 0.04979672 |
| 19 | 632915 | POLRMT | rs12610885 | G | A | 7.28E-06 |

-continued

| CHROM | POS | GENE | SNP ID | REF | ALT | P_FISHER_holm |
|---|---|---|---|---|---|---|
| 2 | 1.79E+3008 | PRKRA | rs75862065 | G | A | 0.000114479 |
| 6 | 1.67E+3008 | PRR18 | rs13205770 | C | T | 6.57E-07 |
| 9 | 33794812 | PRSS3 | rs199873220 | G | T | 1.38E-34 |
| 9 | 33797951 | PRSS3 | rs150316320 | A | C | 2.02E-241 |
| 9 | 33797962 | PRSS3 | rs374178684 | A | G | 3.90E-219 |
| 9 | 33797978 | PRSS3 | rs145485932 | G | A | 1.48E-121 |
| 9 | 33797987 | PRSS3 | rs137945391 | G | T | 4.12E-196 |
| 9 | 33797991 | PRSS3 | rs146966861 | G | A | 1.11E-34 |
| 9 | 33797992 | PRSS3 | rs147593137 | C | T | 2.22E-35 |
| 9 | 33798016 | PRSS3 | rs764430438 | C | T | 6.64E-235 |
| 9 | 33798017 | PRSS3 | rs855581 | A | G | 9.23E-30 |
| 9 | 33799163 | PRSS3 | rs376841271 | C | A | 2.24E-11 |
| 7 | 56087300 | PSPH | rs75395437 | C | T | 1.61E-45 |
| 7 | 56087319 | PSPH | rs73343757 | T | G | 2.76E-40 |
| 7 | 56087364 | PSPH | rs201644817 | G | T | 4.90E-15 |
| 7 | 56087365 | PSPH | rs78067484 | A | G | 7.38E-15 |
| 7 | 56087374 | PSPH | rs200442078 | C | T | 7.82E-16 |
| 7 | 56087379 | PSPH | rs201935398 | T | C | 7.35E-16 |
| 7 | 56087399 | PSPH | rs79321413 | G | A | 0.000433807 |
| 7 | 56087409 | PSPH | rs74874687 | G | A | 0.0006961 |
| 7 | 56088902 | PSPH | rs77329757 | C | T | 1.36E-21 |
| 5 | 36257134 | RANBP3L | rs16902872 | G | A | 0.002050977 |
| 19 | 10431799 | RAVER1 | rs281425 | G | T | 0.00438522 |
| 11 | 63679369 | RCOR2 | rs320108 | T | C | 2.33E-104 |
| 14 | 93154540 | RIN3 | rs71461983 | C | T | 0.04897492 |
| 16 | 11439496 | RMI2 | rs11545336 | G | A | 2.07E-10 |
| 12 | 1.17E+3008 | RNFT2 | rs111256849 | T | C | 0.00408258 |
| 22 | 44369176 | SAMM50 | rs34677401 | G | A | 0.0484264 |
| 2 | 20424573 | SDC1 | rs59231157 | G | A | 0.007829596 |
| 5 | 256472 | SDHA | rs6961 | G | A | 1.24E-06 |
| 15 | 90744960 | SEMA4B | rs11547964 | G | A | 2.66E-06 |
| 1 | 28586376 | SESN2 | rs34315986 | C | G | 0.026956765 |
| 10 | 81372092 | SFTPA1 | rs1059049 | T | C | 0.04210866 |
| 10 | 81372093 | SFTPA1 | rs1059050 | G | A | 0.04210866 |
| 20 | 1592343 | SIRPB1 | rs200963975 | T | C | 1.39E-53 |
| 20 | 1592349 | SIRPB1 | rs777055083 | G | A | 6.13E-88 |
| 11 | 60718792 | SLC15A3 | rs150370599 | C | T | 0.01578615 |
| 2 | 65216886 | SLC1A4 | rs1064512 | G | C | 0.00590105 |
| 2 | 65217089 | SLC1A4 | rs7559202 | G | C | 2.41E-05 |

-continued

| CHROM | POS | GENE | SNP ID | REF | ALT | P_FISHER_holm |
|---|---|---|---|---|---|---|
| 23 | 1.19E+3008 | SLC25A5 | rs77766798 | T | G | 1.87E-08 |
| 23 | 1.19E+3008 | SLC25A5 | rs73637847 | A | G | 1.18E-11 |
| 19 | 49611319 | SNRNP70 | rs1058882 | C | T | 0.001184641 |
| 16 | 50707782 | SNX20 | rs7198294 | C | T | 0.017519256 |
| 2 | 2.31E+3008 | SP140 | rs62192163 | T | C | 1.96E-19 |
| 12 | 1.04E+3008 | STAB2 | rs17034186 | A | G | 8.36E-06 |
| 1 | 1.56E+3008 | SYT11 | rs822522 | G | C | 0.00350393 |
| 1 | 1.56E+3008 | SYT11 | rs822521 | T | C | 0.000737481 |
| 6 | 32821447 | TAP1 | 0 | C | T | 0.015566315 |
| 23 | 9682977 | TBL1X | rs144295789 | C | T | 0.006396936 |
| 22 | 19754091 | TBX1 | rs72646967 | A | C | 0.013366115 |
| 19 | 1010396 | TMEM259 | rs77868901 | G | C | 0.001399827 |
| 19 | 1010406 | TMEM259 | rs62131162 | G | A | 1.31E-05 |
| 12 | 29936613 | TMTC1 | rs184221 | T | G | 1.86E-15 |
| 7 | 5347749 | TNRC18 | rs9639976 | G | A | 0.019363432 |
| 7 | 5352659 | TNRC18 | rs138591330 | G | T | 6.09E-06 |
| 6 | 32011316 | TNXB | 0 | G | T | 0.004192616 |
| 6 | 32011317 | TNXB | 0 | T | C | 0.006396936 |
| 16 | 1279346 | TPSB2 | rs531020024 | G | C | 0.0429312 |
| 7 | 28995800 | TRIL | rs61742220 | G | A | 0.002362389 |
| 3 | 1.5E+3008 | TSC22D2 | rs879634 | G | A | 0.03688618 |
| 1 | 55247097 | TTC22 | rs2286203 | G | A | 2.82E-05 |
| 13 | 31232570 | USPL1 | rs35371042 | T | A | 0.027534 |
| 24 | 15467824 | UTY | rs2032654 | A | G | 0.00992304 |
| 8 | 1.01E+3008 | VPS13B | rs199704158 | A | T | 4.80E-08 |
| 7 | 1.49E+3008 | ZNF467 | rs855667 | G | A | 4.74E-06 |
| 7 | 1.49E+3008 | ZNF467 | rs112589121 | C | T | 5.04E-07 |
| 10 | 1.35E+3008 | ZNF511 | rs3008357 | G | A | 3.97E-10 |
| 19 | 56089947 | ZNF579 | rs10403008 | C | G | 1.35E-05 |
| 14 | 1.03E+3008 | ZNF839 | rs112795025 | G | A | 0.014905632 |

Indicated is the chromosomal location of the variants, their database identifier and the calculated significance as P value.

Example 2: RNA Interference Screen for HRSV Infection Factors

Results from siRNA screens with EGFP reporter virus (RSV-B-05) and F-Luciferase reporter virus (RSV-A-Long) is shown in FIG. 7. Mean scores of three biological replicates are reported. ALN01 is a control siRNA that is directed against RSV. Green arrows mark candidate RSV dependency factors. Knock down of these genes reduces RSV infection. Red arrows mark candidate RSV restriction factors. Knock down of these genes enhances RSV infection. As a result the genes PABPC1, PRKRA, ARSD, MLLT6, and CTDSP2 were identified as dependency factors of HRSV infection, whereas CTBP2, POLRMT, and TMEM259 are restriction factors of HRSV infection.

REFERENCES

Andrews S. (2010). FastQC: a quality control tool for high throughput sequence data. Available online at: bioinformatics.babraham.ac.uk/projects/fastqc Krueger F. (2012). Trim Galore!: A wrapper tool around Cutadapt and FastQC to consistently apply quality and adapter trimming to FastQ files, with some extra functionality for MspI-digested RRBStype (Reduced Representation Bisufite-Seq) libraries. Available online at bioinformatics.babraham.ac.uk/projects/trim_galore/

Alec Wysoker, Kathleen Tibbetts, Tim Fennell (2013): Picard tools version 1.90. Available online at picard.sourceforge.net McKenna A, Hanna M, Banks E, Sivachenko A, Cibulskis K, Kernytsky A, Garimella K, Altshuler D, Gabriel S, Daly M, DePristo M A (2010) The Genome Analysis Toolkit: a MapReduce framework for analyzing next-generation DNA sequencing data. Genome Research 20:1297-303

Cingolani, P. and Platts, A. and Coon, M. and Nguyen, T. and Wang, L. and Land, S. J. and Lu, X. and Ruden, D. M. (2012) A program for annotating and predicting the effects of single nucleotide polymorphisms, SnpEff: SNPs in the genome of *Drosophila melanogaster* strain w1118; iso-2; iso-3. Fly 6(2):80-92. PMID: 22728672

Lek M et al. (2016) Analysis of protein-coding genetic variation in 60,706 humans. Nature 536(7616):285-91. doi: 10.1038/nature19057.

Kircher M, Witten D M, Jain P, O'Roak B J, Cooper G M, Shendure J (2014). A general framework for estimating the relative pathogenicity of human genetic variants. Nat Genet. doi: 10.1038/ng.2892. PubMed PMID: 24487276.

Li H., Handsaker B., Wysoker A., Fennell T., Ruan J., Homer N., Marth G., Abecasis G., Durbin R. and 1000 Genome Project Data Processing Subgroup (2009) The Sequence alignment/map (SAM) format and SAMtools. Bioinformatics, 25, 2078-9. [PMID: 19505943]

The invention claimed is:

1. A method for treatment of a HRSV infection in a subject in need of the treatment, comprising administering to the subject an agonist of transmembrane protein 259 (TMEM259);
   wherein the agonist is an expression construct comprising at least one promoter operably linked to a downstream gene of TMEM259 or a downstream TMEM259 coding region.

2. The method according to claim 1, wherein the HRSV infection is a severe HRSV infection.

3. The method according to claim 1, wherein the HRSV infection is an infection of a human infant, for example of a child between 0 and 5 years, or 0 and 2 years of age.

* * * * *